United States Patent
Seo et al.

(10) Patent No.: US 8,257,557 B2
(45) Date of Patent: Sep. 4, 2012

(54) DEHYDRATION METHOD

(75) Inventors: Tateo Seo, Chiba (JP); Tetsuya Suzuta, Niihama (JP); Toshiaki Ui, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 781 days.

(21) Appl. No.: 12/064,982

(22) PCT Filed: Aug. 29, 2006

(86) PCT No.: PCT/JP2006/317403
§ 371 (c)(1),
(2), (4) Date: Aug. 27, 2008

(87) PCT Pub. No.: WO2007/026911
PCT Pub. Date: Mar. 8, 2007

(65) Prior Publication Data
US 2009/0159422 A1   Jun. 25, 2009

(30) Foreign Application Priority Data

Sep. 1, 2005   (JP) ................................. 2005-253213

(51) Int. Cl.
*B01D 3/34*   (2006.01)
*C07C 37/02*   (2006.01)
*C07C 37/74*   (2006.01)
*C07C 39/04*   (2006.01)

(52) U.S. Cl. ................. 203/12; 203/3; 203/14; 203/18; 203/67; 568/749; 568/796

(58) Field of Classification Search ................ 203/3, 12, 203/14, 18, 67; 568/749, 796; 570/190
See application file for complete search history.

(56) References Cited

U.S. PATENT DOCUMENTS

| | | | |
|---|---|---|---|
| 2,051,782 A * | 8/1936 | Buchheim et al. | 203/18 |
| 3,298,933 A * | 1/1967 | Prahl et al. | 203/39 |
| 3,303,223 A | 2/1967 | Kelly | |
| 4,333,801 A | 6/1982 | Pujado | |
| 4,857,151 A * | 8/1989 | Suciu et al. | 203/82 |
| 2005/0250968 A1 * | 11/2005 | Kawamura et al. | 570/258 |

FOREIGN PATENT DOCUMENTS

| | | |
|---|---|---|
| GB | 392878 | 5/1933 |
| GB | 937272 | 9/1963 |
| JP | 38-18369 B1 | 9/1963 |
| JP | 58-26824 A | 2/1983 |

OTHER PUBLICATIONS

Supplementary European Search Report, dated Jun. 29, 2010, for European Application No. 06797330.5.

* cited by examiner

*Primary Examiner* — Virginia Manoharan
(74) *Attorney, Agent, or Firm* — Birch, Stewart, Kolasch & Birch, LLP

(57) ABSTRACT

A dehydration method for removing water from a hydrolysis reaction mixture containing unreacted water generated when monochlorobenzene is hydrolyzed to produce phenol, the method for dehydrating the hydrolysis reaction mixture includes supplying a hydrolysis reaction mixture to a distillation tower, supplying a liquid containing monochlorobenzene to the tower top portion of the distillation tower, and removing the substantially whole amount of the water in the hydrolysis reaction mixture together with monochlorobenzene from the tower top portion by distillation.

1 Claim, 1 Drawing Sheet

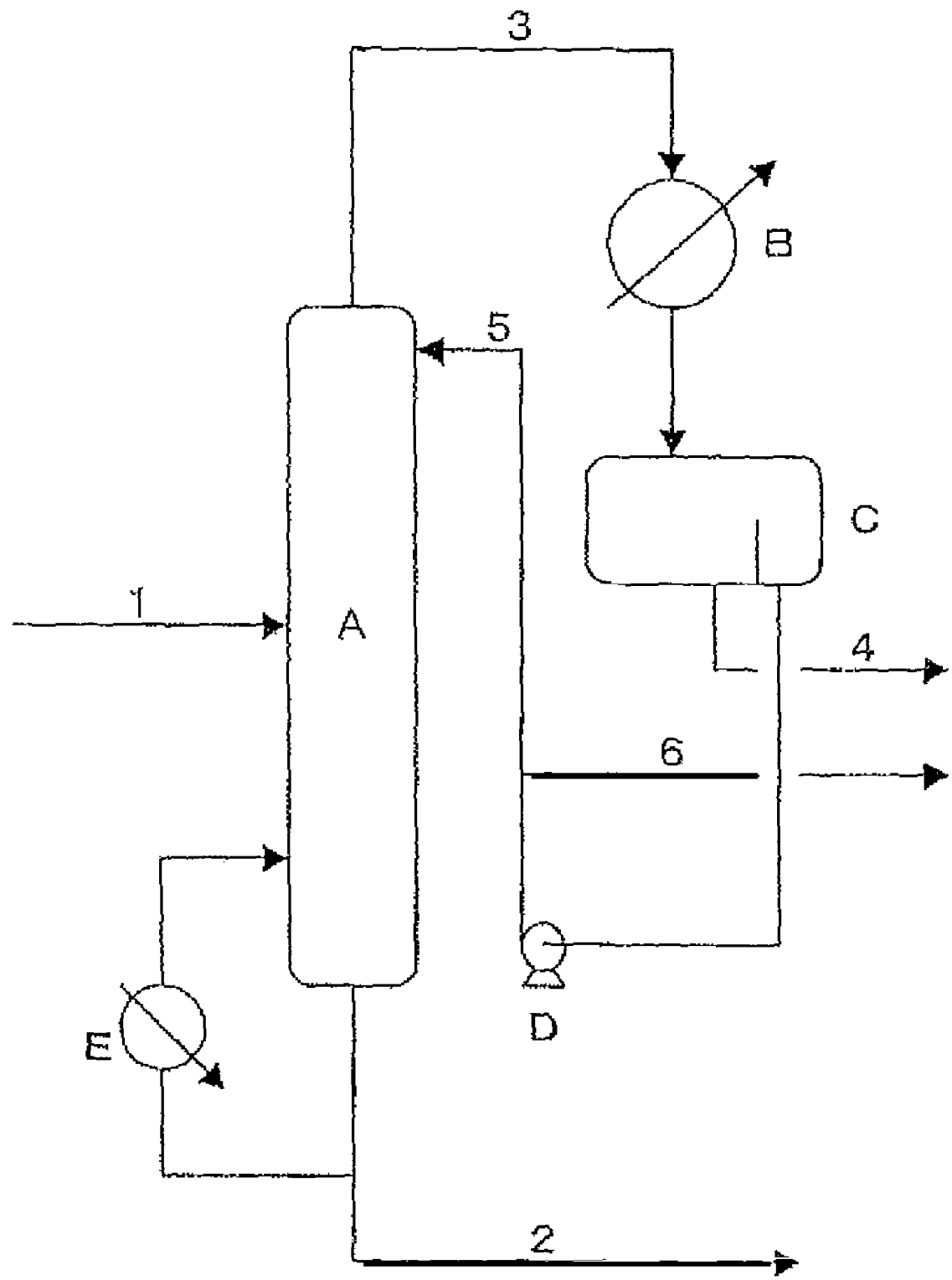

DEHYDRATION METHOD

CROSS-REFERENCE TO RELATED APPLICATIONS

The present application is a national phase under 35 U.S.C. §371 of PCT International Application No. PCT/JP2006/317403 which has an International filing date of Aug. 29, 2006, which claims priority of Application No. 2005-253213 filed in Japan on Sep. 1, 2005 under 35 U.S.C. §119, the entire contents of which are hereby incorporated by reference and for which priority is claimed under 35 U.S.C. §120.

TECHNICAL FIELD

The present invention relates to a method for dehydrating a hydrolysis reaction mixture. More particularly, the present invention relates to a dehydration method for removing water from a hydrolysis reaction mixture containing unreacted water generated when monochlorobenzene is hydrolyzed to produce phenol, the method for dehydrating the hydrolysis reaction mixture being characterized in being capable of highly separating phenol from water and hydrogen chloride through only one distillation operation and having a wide selection range of materials of apparatuses for use in a distillation tower or the like.

BACKGROUND ART

The method for producing phenol by hydrolyzing monochlorobenzene is known (for example, refer to U.S. Pat. No. 3,221,063 and U.S. Pat. No. 3,984,484).

Although the hydrolysis reaction mixture contains unreacted water, unreacted monochlorobenzene, phenol and hydrogen chloride, in order to separate phenol from the hydrolysis reaction mixture, it is necessary to remove water from the hydrolysis reaction mixture.

The above-mentioned known documents disclose a method in which water, hydrogen chloride and phenol in a hydrolysis reaction mixture are condensed and liquefied so as to be separated into a water phase mainly comprising water and hydrogen chloride and an oil phase mainly comprising phenol and monochlorobenzene, and the oil phase is further distilled to separate and collect phenol. However, this method has problems; water and hydrogen chloride are slightly dissolved in the separated oil phase, whereby the operation that is carried out when the oil phase is further distilled becomes complicated, and the selection range of materials of apparatuses for use in a distillation tower or the like is limited in view of corrosion prevention.

DISCLOSURE OF THE INVENTION

Under such circumstances, the present invention is intended to provide a dehydration method for removing water from a hydrolysis reaction mixture containing unreacted water generated when monochlorobenzene is hydrolyzed to produce phenol, the method for dehydrating the hydrolysis reaction mixture being characterized in being capable of highly separating phenol from water and hydrogen chloride through only one distillation operation and having a wide selection range of materials of apparatuses for use in a distillation tower or the like.

In other words, the present invention relates to a dehydration method for removing water from a hydrolysis reaction mixture containing unreacted water generated when monochlorobenzene is hydrolyzed to produce phenol, the method for dehydrating the hydrolysis reaction mixture comprising the steps of supplying a hydrolysis reaction mixture to a distillation tower, supplying a liquid containing monochlorobenzene to the tower top portion of the distillation tower, and removing the substantially whole amount of the water in the hydrolysis reaction mixture together with monochlorobenzene from the tower top portion by distillation.

BRIEF DESCRIPTIONS OF THE DRAWING

FIG. 1 is a flow chart according to Example 1. The numerals denote fluid numbers in Example 1.

A: distillation tower, B and E: heat exchangers, C: liquid separation tank, D: pump

BEST MODES FOR CARRYING OUT THE INVENTION

The following method can be exemplified as a method for obtaining phenol by hydrolyzing monochlorobenzene. A known method can be used as a method for reacting monochlorobenzene with water as described below. The reaction is conducted either under liquid phase or gas phase. The mole ratio of water and chlorinated hydrocarbon (water/chlorinated hydrocarbon) is usually 0.5 or more, the reaction temperature is 600° C. or less, and the reaction pressure is reduced, atmospheric or increased pressure, but usually atmospheric or increased pressure. A supported phosphate catalyst or a supported copper catalyst can be used as a catalyst.

A hydrolysis reaction mixture contains unreacted monochlorobenzene, unreacted water, phenol and hydrogen chloride, usually containing 10 to 90 mole % of water.

In the present invention, a hydrolysis reaction mixture is supplied to a distillation tower, a liquid containing monochlorobenzene is supplied to the tower top portion of the distillation tower, and the substantially whole amount of the water in the hydrolysis reaction mixture is removed together with hydrogen chloride and monochlorobenzene from the tower top portion by distillation. The tower top portion of the distillation tower according to the present invention is defined specifically as a space between the uppermost tray and the vapor outlet at the tower top portion in the case of a tray tower or as a space between the upper surface of the packed portion and the vapor outlet of the tower top portion in the case of a packed tower. It is preferable that the total amount of the monochlorobenzene supplied to the tower top portion of the distillation tower and the monochlorobenzene contained in the hydrolysis reaction mixture is 0.4 moles or more per mole of the water in the hydrolysis reaction mixture supplied to the distillation tower, and that the amount of the monochlorobenzene in the vapor obtained from the tower top portion is 0.39 moles or more per mole of the water in the hydrolysis reaction mixture. If the amount of the monochlorobenzene in the vapor obtained from the tower top portion is extremely smaller than the amount of the water in the hydrolysis reaction mixture, the distillation amount of the water in the hydrolysis reaction mixture cannot be evaporated completely to the tower top portion, whereby a water phase in which hydrogen chloride is dissolved is formed inside the distillation tower and the separation of phenol from water occasionally becomes insufficient. Furthermore, when the water phase is formed inside the tower, the material of the tower is limited to a material having resistance against corrosion by hydrochloric acid, whereby it is difficult to use inexpensive ferrous metal materials.

The substantially whole amount of the water in the hydrolysis reaction mixture means 99.95% or more of the water contained in the hydrolysis reaction mixture. Since the substantially whole amount of the water in the hydrolysis reaction mixture is removed from the tower top portion, the steps of separating phenol from the mixture obtained from the bottom of the tower and purifying the phenol by distillation are simplified; furthermore, even if an inexpensive metal material, such as stainless steel, is used for the apparatuses in these steps, it is possible to have an effect of preventing problems in quality, such as contamination of metal components into the product, i.e., phenol, and coloration of the product.

Preferable specific examples for distillation are as described below.

A hydrolysis reaction mixture is supplied to the middle section of the distillation tower, and water, monochlorobenzene and hydrogen chloride are obtained from the tower top portion, and phenol and monochlorobenzene are obtained from the bottom of the tower. The distillation pressure is between 0.1 to 0.5 PMa during operation. If the pressure is less than 0.1 MPa, the system becomes a reduced-pressure system and the facilities for the system become complicated. If the pressure is more than 0.5 MPa, a high-temperature heat source is necessary as a heat source for heating the bottom of the tower, thereby making the system not economical. Although the distillation temperature is determined by the composition ratios of the components of the hydrolysis reaction mixture and the operating pressure, the temperature is usually 80 to 150° C. at the tower top portion, and 170 to 240° C. at the bottom of the tower. In the case that the amount of the monochlorobenzene in the hydrolysis reaction mixture is less than 0.4 moles per mole of the water in the hydrolysis reaction mixture, monochlorobenzene is additionally supplied to the distillation tower so that the amount of the monochlorobenzene becomes 0.4 moles or more per mole of the water, and the heating amount or the like of the reboiler is adjusted by operation so that the amount of the monochlorobenzene in the vapor obtained from the tower top portion is 0.39 moles or more per mole of the water in the hydrolysis reaction mixture. Although the monochlorobenzene is supplied to the tower top portion of the distillation tower in view of carrying out dehydration efficiently, it may be possible that part thereof is supplied to other positions, such as the supply section for the hydrolysis reaction mixture. The distillation tower may be a tray tower or a packed tower.

The liquid containing monochlorobenzene may be fresh monochlorobenzene or part of the oil phase mainly comprising monochlorobenzene obtained after the water, monochlorobenzene and hydrogen chloride distilled from the tower top portion of the distillation tower, described later, are separated into oil and water phases. Usually, the latter is preferably used.

In order to adjust the amount of the monochlorobenzene in the vapor obtained from the tower top portion to 0.39 moles or more per mole of the water in the hydrolysis reaction mixture, it is preferable that the water, monochlorobenzene and hydrogen chloride distilled from the tower top portion of the distillation tower are separated into a water phase mainly comprising hydrogen chloride and water and an oil phase mainly comprising monochlorobenzene, and that part of the oil phase is supplied to the tower top portion of the distillation tower.

EXAMPLE

Next, the present invention will be described below by way of an example.

Example 1

Into 40 ml of ion-exchanged water, 10.0 g of commercially available copper chloride dihydrate (made by Wako Pure Chemical Industries, Ltd., 99.9 wt % PUA) was added, and the mixture was stirred so that the copper chloride dihydrate was dissolved to prepare an aqueous solution of copper chloride. Into the aqueous solution of copper chloride, 20.0 g of commercially available H-ZSM-5 zeolite (made by N.E. Chemcat Corporation, the weight ratio of Si/Al: 15, 1.6 mm in diameter, extrusion molded) was added and dipped for 8 hours under stirring using a stirrer. The resulting solid content was filtered and washed with ion-exchanged water, dried for 4 hours at 120° C., and burnt for 5 hours at 400° C. to obtain a catalyst. The content of Cu in the obtained catalyst was 3.0 wt % when measured using the alkaline fusion/ICP-AES method.

A fixed bed reactor made of quartz and having an inside diameter of 17 mm was filled with 1 g of the catalyst, and the temperature thereof was maintained at 455° C. To a fixed bed evaporator at 250° C., which is filled with SiC and through which nitrogen gas flows at 11 ml/min, water was supplied at 1.25 g/hr and monochlorobenzene (made by Wako Pure Chemical Industries, Ltd., special grade) was further supplied at 3.21 g/hr, and then the mixture gas produced was supplied to the above-mentioned fixed bed reactor made of quartz to start reaction.

After 1.5 hours, the produced gas was absorbed in toluene as solvent, and the product obtained was analyzed using gas chromatography, and the analysis showed that the monochlorobenzene conversion ratio was 21.7%, that the phenol selectivity was 96.3% and that the benzene selectivity was 2.8%.

The dehydration of a hydrolysis reaction mixture having the same composition as that described above can be carried out optimally according to the flow chart of FIG. 1 and the material balance of Table 1, for example. The gas obtained from the fixed bed reactor is cooled to 175° C. and supplied to the middle section of the distillation tower A (fluid number 1).

The vapor at the tower top portion, mainly comprising hydrogen chloride, water and monochlorobenzene, is cooled and condensed using the heat exchanger B. The condensed liquid is separated into an oil phase mainly comprising monochlorobenzene and a water phase mainly comprising hydrogen chloride and water (hydrochloric acid) using the liquid separation tank C, the water phase is collected (fluid number 4), part of the oil phase is returned to the tower top portion of the distillation tower A using the pump D (fluid number 5), and the remainder in the oil phase is collected (fluid number 6).

The mole ratio of all the monochlorobenzene/water supplied to the distillation tower is 0.69, and the mole ratio of the monochlorobenzene/water in the vapor at the tower top portion is 0.68 (fluid number 3). The distillation tower is operated at a tower top pressure of 0.12 MPa, and the temperature at the tower top portion is 105° C. at this time. By virtue of the operation described above, a liquid (fluid number 2) containing 98% of phenol and not containing water or hydrogen chloride in the gas (fluid number 1) obtained from the fixed bed reactor is collected from the bottom of the distillation tower.

TABLE 1

| | Fluid number | | | | | | |
|---|---|---|---|---|---|---|---|
| | 1 | 2 | 3 | 4 | 5 | 6 | 1 + 5 |
| | Temperature (° C.) | | | | | | |
| | 175 | 180 | 105 | 102 | 102 | 102 | — |
| Pressure (MPa) | 0.15 | 0.15 | 0.12 | 0.12 | 0.12 | 0.12 | — |
| | Molar flow rate (kg-mol/hr) | | | | | | |
| Hydrogen chloride | 420 | 0 | 420 | 420 | 0 | 0 | 420 |
| Water | 4304 | 0 | 4341 | 4267 | 37 | 37 | 4341 |
| Benzene | 12 | 0 | 23 | 1 | 11 | 11 | 23 |
| Monochlorobenzene | 1517 | 49 | 2933 | 3 | 1465 | 1465 | 2982 |
| Phenol | 403 | 396 | 12 | 1 | 6 | 6 | 409 |
| Others | 4 | 4 | 0 | 0 | 0 | 0 | 4 |
| Total | 6660 | 449 | 7730 | 4692 | 1519 | 1519 | 8179 |

INDUSTRIAL APPLICABILITY

The present invention provides a dehydration method for removing water from a hydrolysis reaction mixture containing unreacted water generated when monochlorobenzene is hydrolyzed to produce phenol, the method for dehydrating the hydrolysis reaction mixture being characterized in being capable of highly separating phenol from water and hydrogen chloride through only one distillation operation and having a wide selection range of materials of apparatuses for use in a distillation tower or the like.

The invention claimed is:

1. A dehydration method for removing water from a hydrolysis reaction mixture containing phenol, unreacted monochlorobenzene, hydrogen chloride, and unreacted water generated when monochlorobenzene is hydrolyzed to produce phenol, said method for dehydrating the hydrolysis reaction mixture comprising the steps of supplying a hydrolysis reaction mixture to a distillation tower, supplying a liquid containing monochlorobenzene to the tower top portion of said distillation tower, and removing 99.95% or more of the water in the hydrolysis reaction mixture together with monochlorobenzene in the form of a vapor from said tower top portion by distillation:
   wherein the total amount of the monochlorobenzene supplied to said tower top portion of said distillation tower and the monochlorobenzene contained in the hydrolysis reaction mixture is 0.4 moles or more per mole of the water in the hydrolysis reaction mixture supplied to said distillation tower, and that the amount of the monochlorobenzene in the vapor obtained from said tower top portion is 0.39 moles or more per mole of the water in the hydrolysis reaction mixture,
   wherein the water and monochlorobenzene distilled from said tower top portion of said distillation tower is separated into a water phase mainly comprising water and an oil phase mainly comprising monochlorobenzene, and part of the oil phase is supplied to said tower top portion of said distillation tower, and
   the phenol is separated from the water and the hydrogen chloride through only one distillation operation.

* * * * *